(12) United States Patent
Chong et al.

(10) Patent No.: US 10,482,124 B2
(45) Date of Patent: Nov. 19, 2019

(54) MUSIC RECOMMENDATION BASED ON BIOMETRIC AND MOTION SENSORS ON MOBILE DEVICE

(71) Applicant: Futurewei Technologies, Inc., Plano, TX (US)

(72) Inventors: Chia-Chin Chong, Palo Alto, CA (US); Jianyu Zhang, San Jose, CA (US)

(73) Assignee: Futurewei Technologies, Inc., Plano, TX (US)

( * ) Notice: Subject to any disclaimer, the term of this patent is extended or adjusted under 35 U.S.C. 154(b) by 306 days.

(21) Appl. No.: 15/250,354

(22) Filed: Aug. 29, 2016

(65) Prior Publication Data

US 2016/0371372 A1    Dec. 22, 2016

Related U.S. Application Data

(63) Continuation of application No. 14/040,438, filed on Sep. 27, 2013, now Pat. No. 9,449,084.

(60) Provisional application No. 61/800,380, filed on Mar. 15, 2013.

(51) Int. Cl.

| | |
|---|---|
| *G06F 16/635* | (2019.01) |
| *G06N 20/00* | (2019.01) |
| *G06F 16/638* | (2019.01) |
| *G06F 16/68* | (2019.01) |
| *G06F 16/9032* | (2019.01) |
| *H04H 60/49* | (2008.01) |

(Continued)

(52) U.S. Cl.
CPC .......... *G06F 16/636* (2019.01); *A61B 5/1118* (2013.01); *G06F 3/16* (2013.01); *G06F 3/165* (2013.01); *G06F 16/635* (2019.01); *G06F 16/639* (2019.01); *G06F 16/686* (2019.01); *G06F 16/90324* (2019.01); *G06N 20/00* (2019.01); *H04H 60/33* (2013.01); *H04H 60/46* (2013.01); *H04H 60/49* (2013.01); *H04H 60/65* (2013.01); *A61B 5/01* (2013.01); *A61B 5/02055* (2013.01); *A61B 5/0402* (2013.01); *A61B 5/0476* (2013.01); *A61B 5/4806* (2013.01); *A63B 24/0062* (2013.01); *G06F 16/68* (2019.01)

(58) Field of Classification Search
CPC .............. G06F 3/165; G06F 17/30749; G06F 17/30761; G06F 17/30764; G06F 17/30766; G06F 17/30769; G10L 25/63; H04H 60/12; H04H 60/16; H04H 60/33; H04H 60/35; H04H 60/45; H04H 60/46; H04H 60/49; H04H 60/59; H04H 60/65; A63B 24/0062
USPC .......................................................... 700/94
See application file for complete search history.

(56) References Cited

U.S. PATENT DOCUMENTS

| | | |
|---|---|---|
| 8,442,969 B2 | 5/2013 | Gross |
| 2002/0041692 A1 | 4/2002 | Seto et al. |

(Continued)

OTHER PUBLICATIONS

"Musicovery," downloaded from http://en.wikipedia.org/wiki/Musicovery on Sep. 27, 2013, 4 pgs.

(Continued)

*Primary Examiner* — Jesse A Elbin
(74) *Attorney, Agent, or Firm* — Conley Rose, P.C.

(57) ABSTRACT

A method implemented by a mobile device for music recommendation to a user of the mobile device, the method comprising acquiring one or more measurements from at least one biometric sensor to obtain biometric information of the user, determining a music based at least in part on the biometric information, and recommending the music to the user for playing.

17 Claims, 5 Drawing Sheets

(51) Int. Cl.

| | |
|---|---|
| *H04H 60/33* | (2008.01) |
| *H04H 60/46* | (2008.01) |
| *H04H 60/65* | (2008.01) |
| *A61B 5/11* | (2006.01) |
| *G06F 3/16* | (2006.01) |
| *A63B 24/00* | (2006.01) |
| *A61B 5/01* | (2006.01) |
| *A61B 5/0205* | (2006.01) |
| *A61B 5/0402* | (2006.01) |
| *A61B 5/0476* | (2006.01) |
| *A61B 5/00* | (2006.01) |

(56) References Cited

U.S. PATENT DOCUMENTS

| | | |
|---|---|---|
| 2007/0113725 A1 | 5/2007 | Oliver et al. |
| 2008/0096726 A1 | 4/2008 | Riley et al. |
| 2009/0006288 A1 | 1/2009 | Yamamoto |
| 2009/0069912 A1 | 3/2009 | Stefik |
| 2009/0076637 A1 | 3/2009 | Kameyama |
| 2011/0093100 A1 | 4/2011 | Ramsay |
| 2011/0169603 A1 | 7/2011 | Fithian et al. |
| 2012/0229270 A1 | 9/2012 | Morley et al. |
| 2014/0119564 A1 | 5/2014 | Caskey et al. |

OTHER PUBLICATIONS

"Pandora Radio," downloaded from http://en.wikipedia.org/wiki/Pandora_Radio on Sep. 27, 2013, 10 pgs.

"Spotify," downloaded from http://en.wikipedia.org/wiki/Spotify on Sep. 27, 2013, 17 pgs.

"User:Yuhamidaru/stereomood," downloaded from http://en.wikipedia.org/wiki/User:Yuhamidaru/stereomood on Sep. 27, 2013, 3 pgs.

Shardanand, U., "Social Information Filtering for Music Recommendation," Massachusetts Institute of Technology, Sep. 1994, pp. 1-93.

Kuo, F.-F., "Emotion-based Music Recommendation by Association Discovery from Film Music," MM'05 Nov. 6-11, 2005, Singapore, 2005 ACM, pp. 507-510.

Fitchard, K., "How Gracenote is building a Car Stereo that senses your driving mood," downloaded from http://gigaom.com/2013/02/19/how-gracenote-is-building-a-car-stereo-that-senses-your-driving-mood/ on Sep. 30, 2013, 4 pages.

Office Action dated Sep. 10, 2015, 21 pages, U.S. Appl. No. 14/040,438, filed Sep. 27, 2013.

Notice of Allowance dated May 20, 2016, 8 pages, U.S. Appl. No. 14/040,438, filed Sep. 27, 2013.

Office Action dated Feb. 4, 2016, 22 pages, U.S. Appl. No. 14/040,438, filed Sep. 27, 2013.

Office Action dated Apr. 13, 2016, 5 pages, U.S. Appl. No. 14/040,438, filed Sep. 27, 2013.

Office Action dated Mar. 17, 2016, 20 pages, U.S. Appl. No. 14/040,436, filed Sep. 27, 2013.

Office Action dated Sep. 17, 2015, 22 pages, U.S. Appl. No. 14/040,436, filed Sep. 27, 2013.

Notice of Allowance dated May 20, 2016, 8 pages, U.S. Appl. No. 14/040,436, filed Sep. 27, 2013.

Office Action dated Oct. 16, 2015, 14 pages, U.S. Appl. No. 14/142,249, filed Dec. 27, 2013.

MUSIC RECOMMENDATION BASED ON BIOMETRIC AND MOTION SENSORS ON MOBILE DEVICE

CROSS-REFERENCE TO RELATED APPLICATIONS

The present application is a continuation of U.S. patent application Ser. No. 14/040,438 filed Sep. 27, 2013 by Chia-Chin Chong et al. and entitled "Music Recommendation Based on Biometric and Motion Sensors on Mobile Device", which claims priority to U.S. Provisional Patent Application No. 61/800,380 filed Mar. 15, 2013 by Chia-Chin Chong et al. and entitled "Motion-based Music Recommendation System, Method and Service for Mobile Devices", both of which are incorporated herein by reference in their entireties.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Music recommendation has been around for sometime. Music recommendation systems and services, such as those known as Pandora, Ringo, Spotify, Musicovery, Steremood, are becoming increasingly popular ways for users to find and listen to music that may be of interest to them. Most of these music recommendation systems may identify and recommend a music to a user based on the user's personal preference, which may be indicated by the user through manual selection or some other type of affirmative action by the user to indicate the user's preferences (e.g., hitting a "like" or "dislike" button).

For example, Pandora is a personalized internet radio service. The service plays musical selections of a certain genre based on an artist selection by a user or subscriber of the service. To improve the music recommendation system over time, the user can provide positive or negative feedback for songs chosen by the service, which are taken into account when Pandora selects or recommends future songs to the user.

Ringo is another music recommendation system that may be accessed by users via email. Users may rate musical artists and then may be able to receive recommendations for further songs to listen to.

Spotify is yet another way to enjoy music socially. Spotify may not recommend songs based on individual preferences, but Spotify may instead allow registered users to integrate their user account with other social accounts (e.g., Facebook and Twitter accounts). Once a user integrates his or her Spotify account with other social media profiles, the user may access favorite music and playlists of his or her friends. Further, Spotify allows the user to share songs and playlists with his or her friends, and even work together on collaborative playlists.

Musicovery is yet another music recommendation system that has a collection of songs in its "Mood Radio". On a homepage, music may be marked with one of four basic moods: Dark, energetic, positive, and calm. A user may choose his or her era, and share his or her mood with his or her favorite songs.

Steremood is yet another music recommendation system that may set "tags" to represent a variety of emotions. Users can choose from tags that most accurately define their emotional state.

However, some existing music recommendation systems and services such as those mentioned above may be relatively inflexible, since they may not take into account the fact that music preferences of a user using a mobile device may change over time as physical conditions of the user changes. Mobile device users often use their devices on the go while engaging in various activities and entering various environments, thus their music listening preferences may change from moment to moment. Requiring users to manually set or change their personal music listening preferences on their mobile devices can be inconvenient, as user preferences may change frequently among different activities or environments. Further, the limited user interface provided by most mobile devices may make manual setting more inconvenient. Accordingly, there exists a need for a music recommendation system or service that better considers the changing music preferences of a user.

SUMMARY

In one embodiment, the disclosure includes a method implemented by a mobile device for music recommendation to a user of the mobile device, the method comprising acquiring one or more measurements from at least one biometric sensor to obtain biometric information of the user, determining a music based at least in part on the biometric information, and recommending the music to the user for playing.

In another embodiment, the disclosure includes a mobile device comprising a processor configured to couple to at least one biometric sensor and further configured to acquire one or more measurements from the at least one biometric sensor to obtain biometric information of the user, determine a music based at least in part on the biometric information, and recommend the music to the user for playing.

In yet another embodiment, the disclosure includes a computer program product comprising computer executable instructions stored on a non-transitory computer readable medium such that when executed by a processor cause a mobile device to acquire one or more measurements from the at least one sensor to obtain physical condition data of a user using the mobile device, determine a music based at least in part on the physical condition data, and recommend the music to the user for playing.

These and other features will be more clearly understood from the following detailed description taken in conjunction with the accompanying drawings and claims.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION OF ILLUSTRATIVE EMBODIMENTS

It should be understood at the outset that although illustrative implementations of one or more embodiments are provided below, the disclosed systems and/or methods may be implemented using any number of techniques, whether currently known or in existence or contemplated in the future. The disclosure should in no way be limited to the illustrative implementations, drawings, and techniques illustrated below, including the exemplary designs and implementations illustrated and described herein.

In view of the limitations of existing music recommendation systems and services as described above, the inventors of the subject application have recognized a need for a personalized and automatic music recommendation system, method, and service for mobile devices such as smartphones that takes into account the mobile device user's physical condition or state.

The present disclosure teaches automatic music recommendation based on physical condition of a user. A mobile device may make automatic music recommendation to a user using the mobile device based on his or her physical motions and/or biometric information. In at least some embodiments, the disclosed music recommendation system exploits sensors that may exist on or be coupled to mobile devices, and combines them with mood-based music classification to make personalized music recommendations based on the user's physical condition. The physical condition of the user may include physical motion of the user, or biometric information of the user, or both. The system may map the physical condition of the user to a mood of the user through a context awareness platform learning system.

The type of music or song to be recommended to the user may be based on the users' mood categories, which can be obtained from a context awareness platform in the mobile device. In this manner, the disclosed music recommendation method and system may quickly and automatically adapt recommendations according to changes in the user's physical condition, such as activities, environments, and/or biometric states. Further, the disclosed music recommendation system may not require manual intervention or express action by the user, which may prove a convenient feature for mobile devices. The disclosed music recommendation system may still be capable of taking feedback from the user to improve music recommendation to better suit the user's preferences.

Illustrative embodiments of the automatic personalized music recommendation method, system, and service are described in more detail below. While music recommendation is mostly discussed in the context of a mobile communications device such as a smartphone, it may be implemented on any portable electronic device capable of playing music (e.g., portable media player, tablet computer, wrist computer, etc.). The portable electronic device may be equipped with or coupled to physical and/or virtual sensors. Also, although the illustrative embodiments of music recommendation are implemented in a mobile device, one of ordinary skill in the art could readily implement the method as a cloud-based service for a mobile device. Further, although illustrative embodiments are described in the context of recommending music content to the user, one of ordinary skill in the art could readily adapt the method to recommending other types of content to the user, such as videos, animated graphics, web sites, etc.

Figure 1:
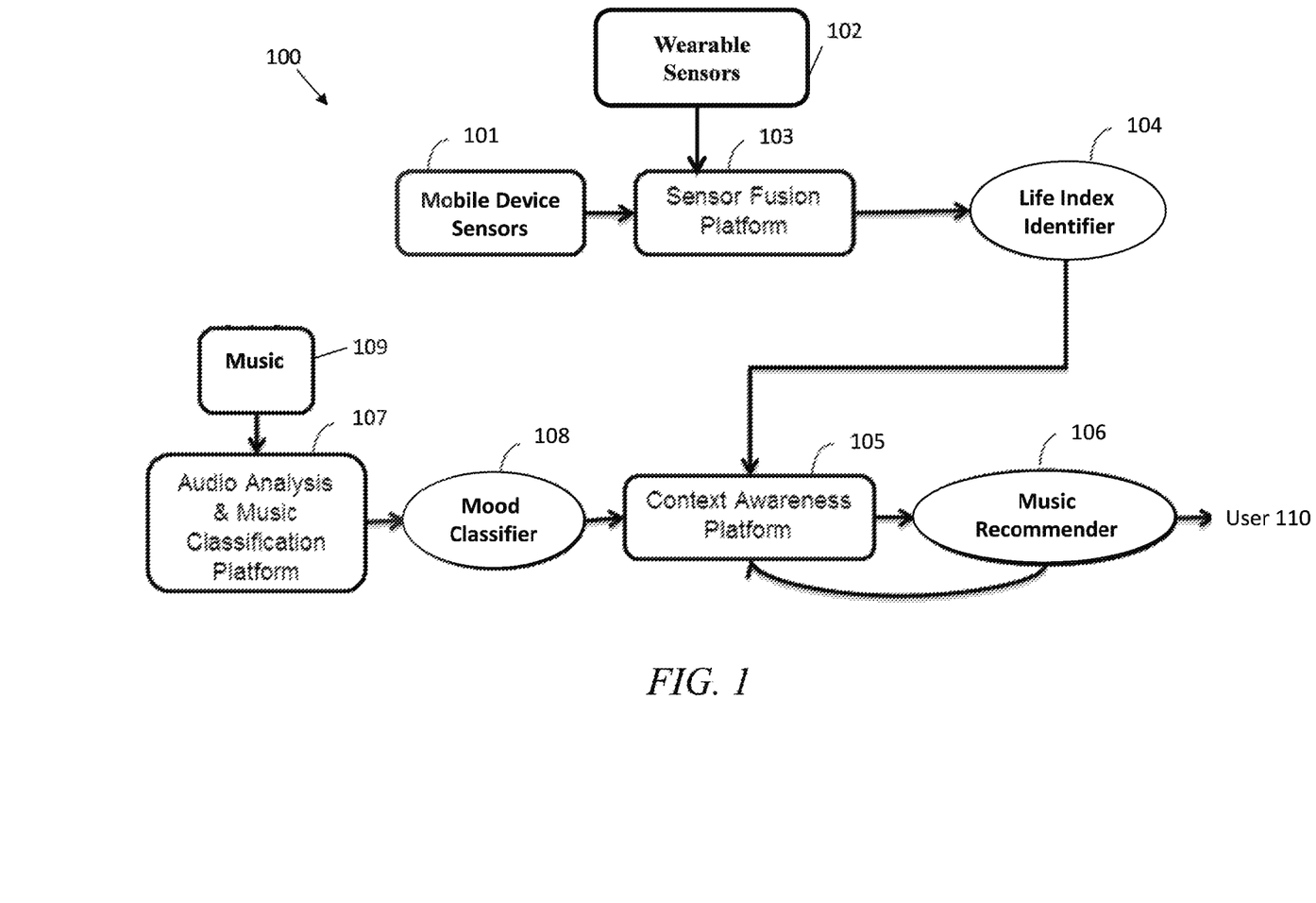
FIG. 1 is a schematic diagram of an embodiment of a music recommendation system.

FIG. 1 is a schematic diagram of an embodiment of a music recommendation system 100, in which disclosed embodiments may operate. The music recommendation system 100 may represent an overall structure and function of an embodiment of the automatic and personalized music recommendation method, system and service. The music recommendation system 100 may be implemented on a mobile device, which may be any portable device capable of playing music. Examples of mobile devices include, but are not limited to, smartphone, tablet, portable media player (PMP), tablet computer, wrist computer, etc.

The system 100 includes one or more mobile device sensors 101, one or more wearable device sensors 102, a sensor fusion platform 103, a context awareness platform 105, an audio analysis and/or music classification platform 107, and a music database 109, arranged as shown in FIG. 1. The system 100 may further use a life index identifier (sometimes interchangeably referred to as a wellness identifier) 104, a music recommender 106, and a mood classifier 108 when recommending music to a user 110. The platforms, modules, units, databases, and data structures may work together as indicated to automatically provide personalized music recommendations to the user 110 of the mobile device.

In use, the mobile device sensors 101 may be embedded or integrated as physical and/or virtual sensors in a mobile device, while the wearable device sensors 102 may be coupled, either wirelessly or through wires, to a mobile device. There may be sensors that collect physical motion data, or biometric information or data, or both. Exemplary biometric information includes skin temperature, heart rate patterns, perspiration level, etc. The biometrics information of the users can be obtained based on the data collected from biometric sensors. Examples of biometric sensors include, but are not limited to, temperature sensor, heart rate sensor, sweat sensor, etc.

The biometric sensors may be embedded on the mobile device, or coupled wired or wirelessly to the mobile device through third-party wellness wearable devices (e.g., those made by or known as Nike, Fuelband, Jawbone UP, and FitbitFlex). With the increasing popularity of wearable devices that can collect biometric information (e.g., heart rate, perspiration, skin temperature) from users, these data can be sent to (e.g., by syncing) a mobile device to provide intelligent recommendations and services, such as biometric-based music recommendation. Body biometrics of the user may change when the user engages in different activities or enters different environments.

Similarly, physical motion of the users can be obtained based on the data collected from motion sensors. Examples of motion sensors include, but are not limited to, accelerometers, gyroscopes, pressure sensors, etc. The motion sensors may be embedded on the mobile device, or be coupled to the mobile device wired or wirelessly. Physical motion of the user may change when the user engages in different activities.

The sensor fusion platform 103 may include sensor data analysis and post-processing and sensor fusion classification. Sensor data analysis may be implemented using a Kalman filter (i.e., linear quadratic estimation) or other type of filtering as is well known in the art. Sensor fusion classification may be implemented using Bayesian models, hidden Markov models, neural networks, etc. The sensor fusion platform 103 may be implemented as a module or computer program instructions in a computing system, such as a mobile device.

By utilizing the sensor fusion platform 103, raw data collected from the motion and wearable sensors 101 and 102 can be inferred into various physical and wellness categories such as sitting, walking, running, driving, anxiety, stress, fatigue, etc. Specifically, an activity identifier may be determined based on physical motion data as a classification of a physical motion or activity of the user, and a biometric identifier may be determined based on the biometric information as a classification of a biometric state of the user. An activity identifier may be implemented as a table of possible physical activities that will be inferred by sensor fusion platform 103 based on sensing data collected from sensors 101 and/or 102. These physical activities may include sitting, walking, running, driving, etc. Similarly, a biometric identifier may be implemented as a table of possible biometric states that will be inferred by sensor fusion platform 103 based on sensing data collected from sensors 101 and/or 102. These biometric states may include heart rate pattern, skin temperature, perspiration level, oxygen level, brain wave, actigraphy sleep pattern, electrocardiography (ECG, sometimes referred to as EKG), etc.

Further, the wellness identifier or life index identifier 104 may be determined combining or jointly based on the activity identifier and the biometric identifier as an indication of the physical condition of the user. The sensor fusion platform 103 and the life index identifier 104 work together to accept sensor data from sensors 101 and 102 in a mobile device.

The life index identifier 104 for the user 110 may be provided by the sensor fusion platform 103, and may feed into the context awareness platform 105 to generate the music recommender 106 for the user 110. By using the context awareness platform 105 to learn and understand music preferences of the user 110 in each physical and wellness category which is identifiable by the life index identifier 104, the music recommender 106 may be automatically generated in response to the life index identifier 104.

The mood classifier 108 may be implemented as a table of possible moods (or emotional states) that can be used to classify each of the songs or audio files. These moods could include happy, ecstatic, content, sad, depressed, nervous, angry, bored, tired, hyper, excited, grumpy, aggressive, etc. The music recommender 106 may be implemented as a table of possible music types or genres that are provided as input to the context awareness platform 105. These music types could include alternative, blues, classical, country, club, house, folk, heavy metal, hip-hop, jazz, Latin, pop, reggae, rock, etc.

The music recommender 106 may classify songs into different moods, which may be identifiable via the mood classifier 108. Thus, a music category or type of song to be recommended to the user 110 may be based on the mood of the user 110. The mood can be obtained from the context awareness platform 105 in the mobile device, e.g., after processing and learning the users' physical motion and biometric data over time. Further, the music recommender 106 may be a learning system that takes feedback from the user 110 and improves its recommendation accuracy over time with increased training.

In an embodiment, the context awareness platform 105 may include the following three components: (1) user intent/inference/prediction, (2) user model/situational model and (3) machine learning. The user model component includes: (1) a user model specifying significant locations, time patterns, preferences and relations, (2) user model algorithms and (3) user behavior modeling. The situational model component includes: (1) a situational model specifying current locations, time relation, motion status, active relationships, current activity, (2) situational model algorithms and (3) context modeling.

A music may exist in any form, e.g., as an audio file or files, media file, in the music database 109 and may comprise any content (not limited to songs but may include speeches, other sounds, etc.). The music database 109 may be stored anywhere, e.g., locally on the mobile device, or in a cloud storage, or both. Further, it is possible that other parts of the system 100 such as the audio analysis and/or music classification platform 107, the mood classifier 108, the context awareness platform 105, and/or the music recommender 106 exist in the cloud. In this case, mood classification of music may be performed offline and a user profile may be built over time and stored offline in the cloud. The sensors 101 and 102 may still be in or coupled to the mobile device, and physical condition identification may still take place in the mobile device. Output from the life index identifier 104 and any user feedback may be provided to an application running in the cloud that accepts the inputs. The cloud application may make a selection and stream the selection to the mobile device. Note that FIG. 1 may be combined with more drawings and descriptions below to further understand working principles of embodiments disclosed herein.

Figure 2:
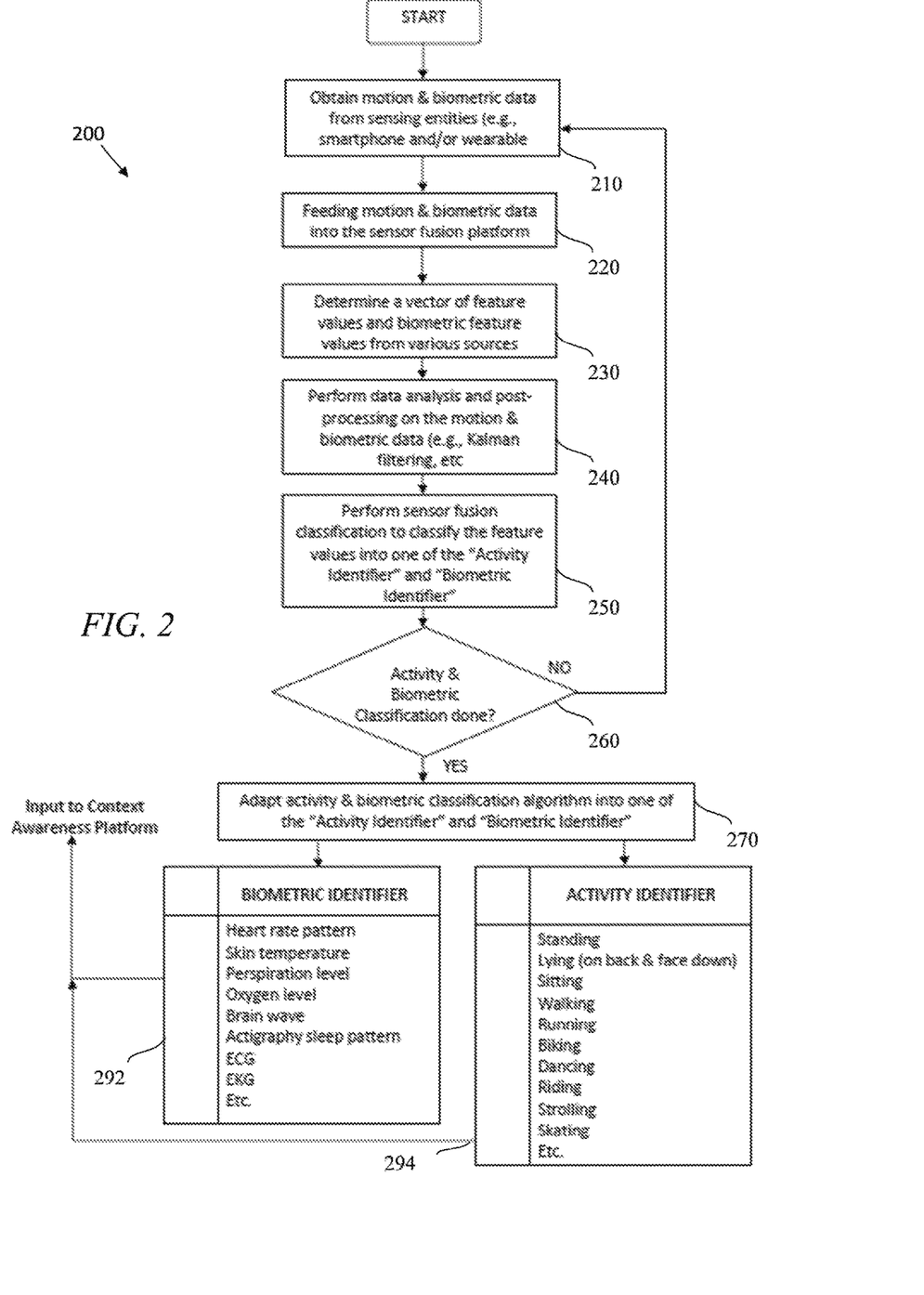
FIG. 2 a flowchart of an embodiment of a method on how raw data obtained from the sensors can be analyzed.
Figure 3:
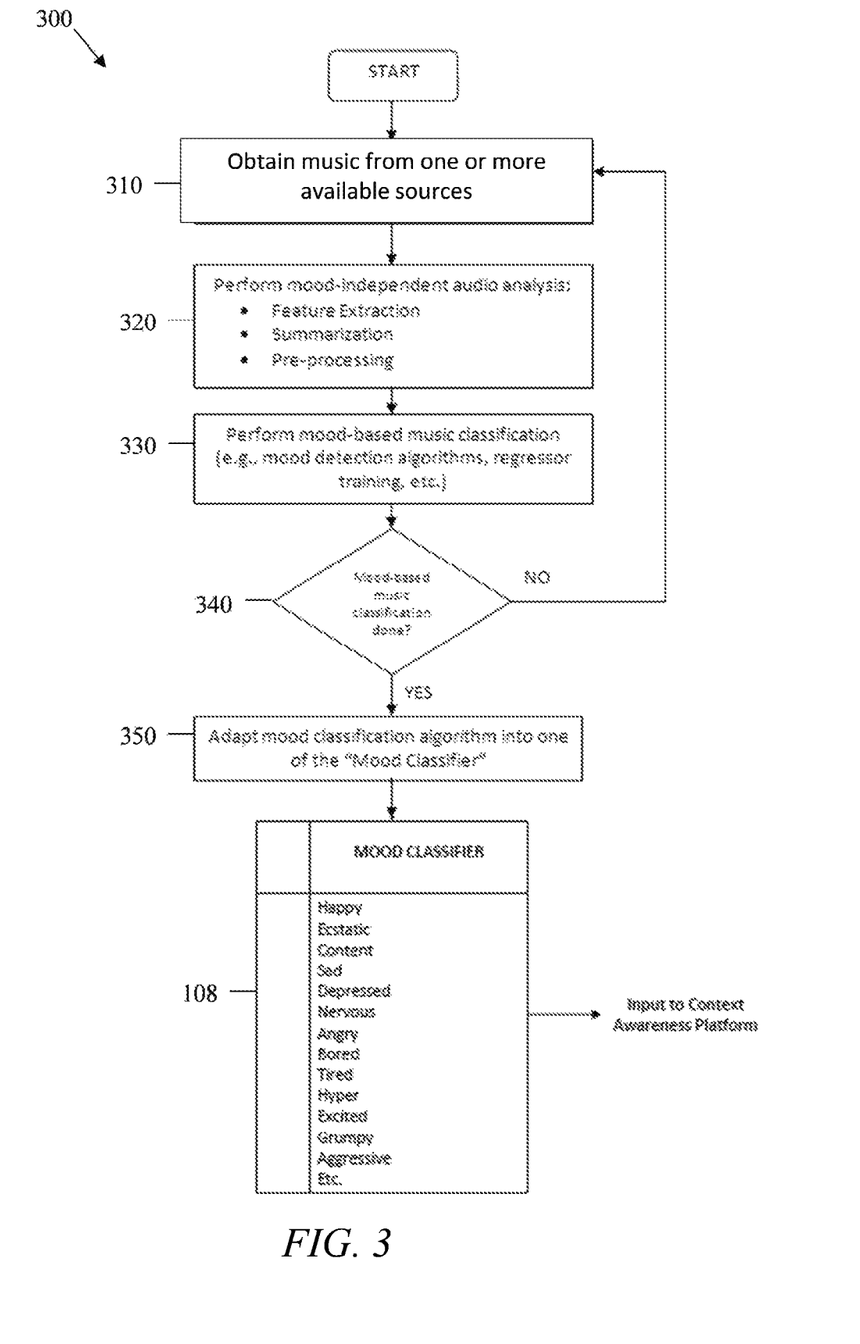
FIG. 3 is a flowchart of an embodiment of a method for classifying music into one or more moods.
Figure 4:
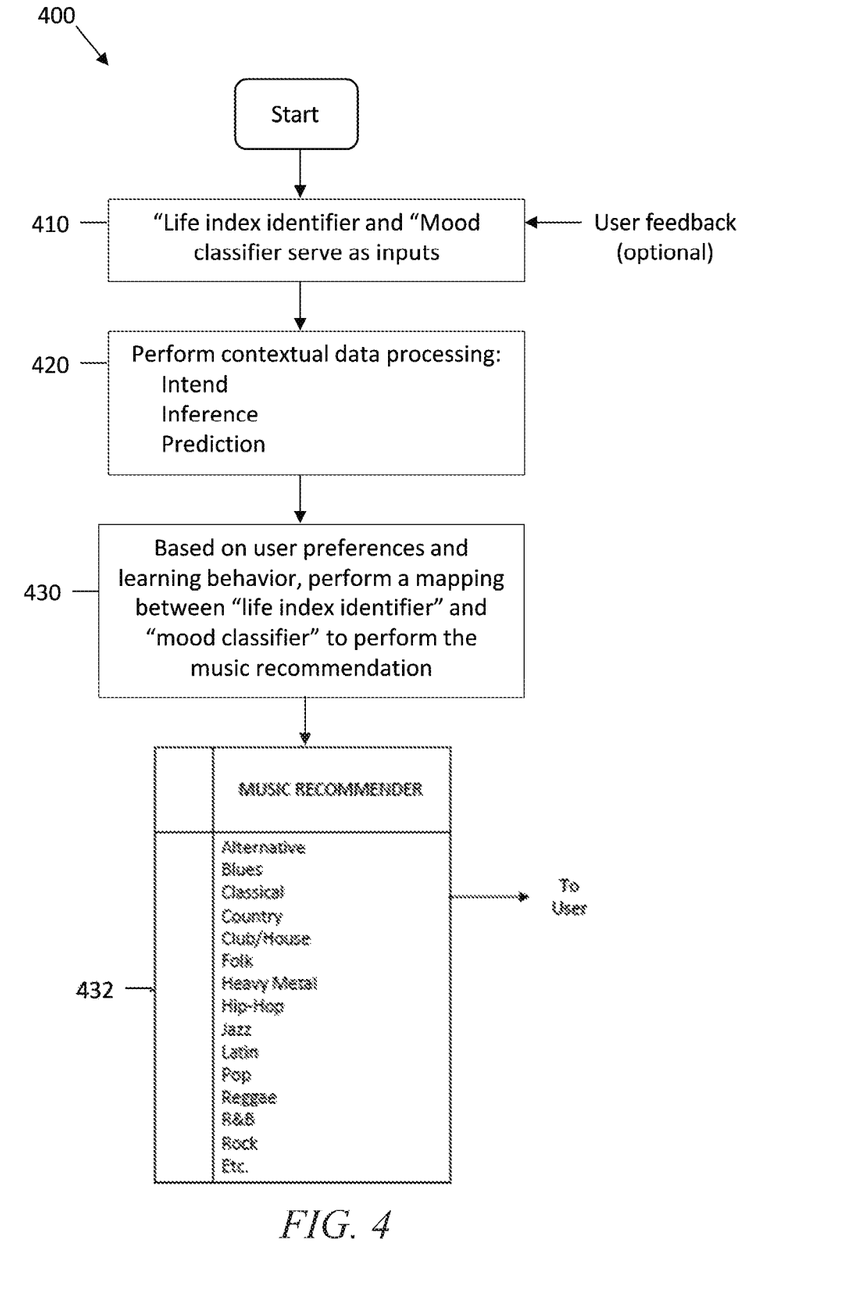
FIG. 4 is a flowchart of a method for music recommendations to a user.

FIGS. 2, 3 and 4 are flowcharts showing an overall process in which the music recommendation method, system and service shown in FIG. 1 generates music recommendations to the user 110 based on sensor input and user preference (e.g., intent, inference, and/or prediction) of the context awareness platform 105.

Specifically, FIG. 2 a flowchart of an embodiment of a method 200 on how raw data obtained from the sensors 101 and 102 may be analyzed and processed by the sensor fusion platform 103 to generate the vector of feature values, which will then be classified by sensor fusion platform 103 into life index identifier 104.

The method 200 starts in step 210, in which a music recommendation system (e.g., the system 100) may acquire one or more measurements to obtain motion and biometric data from sensing entities (e.g., the sensors 101 and 102 which may include motion sensors and biometric sensors). In step 220, the motion data and biometric information may be fed into the sensor fusion platform 103. In step 230, the system 100 may determine a vector of feature values and biometric feature values from various sources. In step 240, data analysis and post-processing of the sensing data may be performed. In this step, Kalman filtering and other signal processing may be performed on the data, e.g., to determine a pattern of speed and/or orientation and/or motion. Feature values of the underlying data may be determined. In step 250, the results of step 240 are used to classify a sensor measurement regarding the user into one of the activity identifiers or biometric identifiers, e.g., one of the biometric identifiers listed in block 292, or one of the activity identifiers listed in block 294.

In step 260, a decision is made whether activity and biometric classification is complete. A determination of whether it is complete may be based on whether sufficient data has been collected to provide confidence in the activity classification or biometric classification, or it may be based on whether a sufficient amount of time has passed since sensor data collection began. If activity classification is complete, step 270 is performed, in which an activity and biometric classification algorithm may be adapted into one of the activity identifier and biometric identifier.

Further, an activity identifier and a biometric identifier may be combined or jointed to determine a life index identifier (e.g., the life index identifier 104). The life index identifier 104 may be provided as an input to the context awareness platform 105. If classification is not complete in step 260, the flowchart returns to step 210 in which more sensing data is collected.

FIG. 3 is a flowchart of an embodiment of a method 300 for classifying music (e.g., an audio file) into one or more moods. The method 300 shows how music files are obtained & sorted in order to perform both the mood-independent audio analysis & mood-based music classification in audio analysis and/or music classification platform 107 (or "platform 107"), which may then be classified by the platform 107 into the mood classifier 108. The method 300 begins in step 310. In step 310, music may be obtained from available sources, such as from cloud storage, local storage on a mobile device, etc. The platform 107 may receive one or more audio files as inputs. In step 320, mood-independent audio analysis is performed, which may include feature extraction, summarization, and pre-processing of the audio signal represented by an audio file. In step 330, mood-based music classification may be performed, e.g., using mood detection algorithms or regressor training in order to map or classify an audio file into one or more of the moods in the mood classifier 108. In decision step 340, a decision is made whether mood-based classification is complete. If classification is complete, a mood classifier 108 is selected in step 350 for the audio files. After this process, an audio file will have at least one associated mood.

FIG. 4 is a flowchart of a method 400 on how life index identifier 104 and mood classifier 108 may be used as inputs to context awareness platform 105 in order for music recommender 106 to generate music recommendations for the user. In step 410, a life index identifier (e.g., life index identifier 104) and a mood classifier (e.g., mood classifier 108) may serve as inputs. These inputs may be derived as shown in FIGS. 2 and 3. A context awareness platform may acquire or receive the inputs. In step 420, a machine-learning algorithm is performed that learns how to correlate activity to mood based on user feedback (if any). At the outset before any user feedback, the method 400 includes a set of initial conditions that correlates or maps user activity to mood. In step 430, a mapping of life index identifier to mood classifier is performed which is used to generate a music recommendation. In summary, in at least one embodiment sensor data leads to a user life index classification which maps to a mood which maps to a music genre (e.g., those defined in the block 432) which provides a music recommendation.

Figure 5:
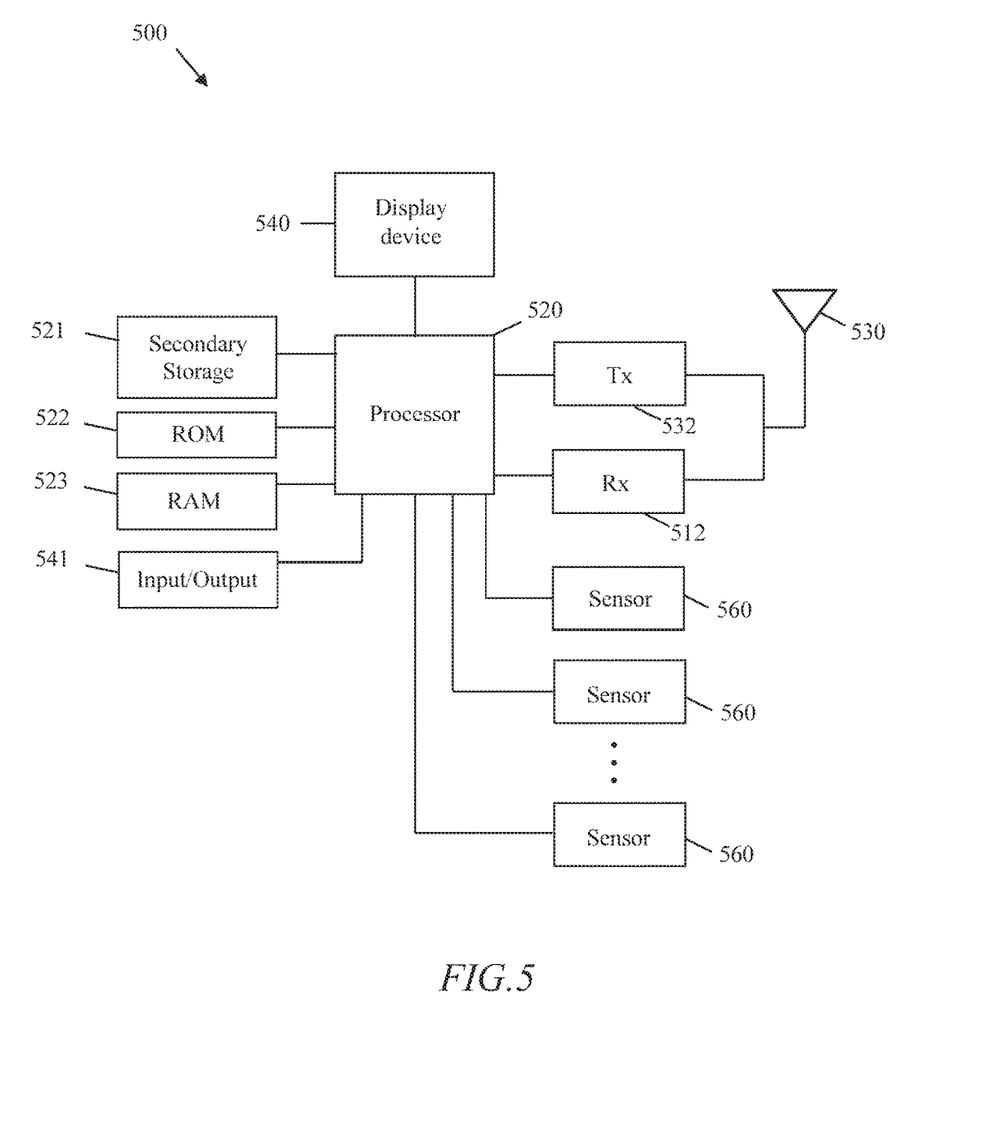
FIG. 5 is a block diagram of a mobile device that may be used to implement the music recommendation method and system disclosed herein.

FIG. 5 is a block diagram of a mobile device 500 that may be used to implement the music recommendation method and system disclosed herein. Mobile device 500 may comprise a processor 520 (which may be referred to as a central processor unit or CPU) that is in communication with memory devices including secondary storage 521, read only memory (ROM) 522, and random access memory (RAM) 523. The processor 520 may be implemented as one or more general purpose CPU chips, one or more cores (e.g., a multi-core processor), one or more application specific integrated circuits (ASICs) and/or one or more digital signal processors (DSPs). The processor 520 may be configured to implement any of the schemes described herein, and may be implemented using hardware, software, firmware, or combinations thereof.

The secondary storage 521 may be comprised of one or more solid state drives, disk drives, and/or other memory types and is used for non-volatile storage of data and as an over-flow data storage device if RAM 523 is not large enough to hold all working data. Secondary storage 521 may be used to store programs that are loaded into RAM 523 when such programs are selected for execution. The ROM 522 may be used to store instructions and perhaps data that are read during program execution. ROM 522 may be a non-volatile memory device with a small memory capacity relative to the larger memory capacity of secondary storage 521. The RAM 523 may be used to store volatile data and perhaps to store computer instructions. Access to both ROM 522 and RAM 523 may be faster than to secondary storage 521.

The mobile device 500 may communicate data (e.g., packets) wirelessly with a network via a network access point (not shown). As such, the mobile device 500 may comprise a receiver (Rx) 512, which may be configured for receiving data (e.g. wireless packets or frames) from other components. The receiver 512 may be coupled to the processor 520, which may be configured to process the data and determine to which components the data is to be sent. The mobile device 500 may also comprise a transmitter (Tx) 532 coupled to the processor 520 and configured for transmitting data to other components, for example by using protocols such as Institute of Electrical and Electronics Engineers (IEEE) 802.11, IEEE 802.16, 3rd Generation Partnership Project (3GPP), Global System for Mobile Communications (GSM), or similar wireless protocols. The receiver 512 and transmitter 532 may be coupled to at least one antenna 530, which may be configured to receive and transmit wireless radio frequency (RF) signals. In some embodiments, Tx 532 and Rx 512 may be replaced by a transceiver comprising the functionality of both Tx 532 and Rx 512. If the context awareness platform 105 and logic for selecting an audio file based on activity identifier is located in a cloud-based application, the Tx 532 may be used to communicate the activity identifier to the cloud-based application. The cloud-based application may return an audio file selection. The audio file selection may be stored on the mobile device in, e.g., secondary storage 521 or the audio file selection may be stored in a cloud-based storage application. If audio files (e.g., some or all of music database 109) are stored remotely, the Rx 512 may be used to receive audio files.

The mobile device 500 may also comprise a display device 540 coupled to the processor 520, that displays output thereof. The mobile device 500 and the display device 540 may be configured to display representations of data, which may be visible to a user. The display device 540 may comprise a color super twisted nematic (CSTN) display, a thin film transistor (TFT) display, a thin film diode (TFD) display, an organic light-emitting diode (OLED) display, an active-matrix OLED display, or any other display screen. The display device 540 may display in color or monochrome and may be equipped with a touch sensor based on resistive and/or capacitive technologies.

The mobile device 500 may further comprise an input/output (I/O) device 541 coupled to the processor 520, which may allow the user to input commands to the mobile device 500. Although labeled as a single device, the I/O device 541 may comprise multiple devices. In the case that the display device 540 comprises a touch sensor, the display device 540 may also be considered the I/O device 541. In addition to and/or in the alternative, an I/O device 541 may comprise a mouse, trackball, built-in keyboard, external keyboard, and/or any other device that a user may employ to interact with the mobile device 500. The I/O device 541 may comprise one or more speakers or headset jacks for providing audio signals. The processor 520 may convert a digital audio file to an analog audio signal for transmission via the I/O device 541 to be enjoyed by a user.

The mobile device 500 may further comprise one or more sensors 560, such as the sensors 101 and 102 described previously. The sensors 560 may include accelerometers, magnetometers, gyroscopes, pressure sensors, and/or a Global Positioning System (GPS) device as examples. The sensors 560 provide sensor data to the processor 520.

It is understood that by programming and/or loading computer executable instructions onto the mobile device 500, at least one of the processor 520, memory 521-523, and/or Rx/Tx 512/532 are changed, transforming the mobile device 500 in part into a particular machine or apparatus, e.g., one or more mobile device sensors 101, one or more wearable device sensors 102, a sensor fusion platform 103, a context awareness platform 105, an audio analysis and/or music classification platform 107, a music database 109, a wellness identifier 104, a music recommender 106, and a mood classifier 108 as described herein. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an ASIC, because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations may be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_1$, and an upper limit, $R_u$, is disclosed, any number falling within the range is specifically disclosed. In particular, the following numbers within the range are specifically disclosed: $R=R_1+k*(R_u-R_1)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. The use of the term "about" means+/−10% of the subsequent number, unless otherwise stated. Use of the term "optionally" with respect to any element of a claim means that the element is required, or alternatively, the element is not required, both alternatives being within the scope of the claim. Use of broader terms such as comprises, includes, and having may be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure. The discussion of a reference in the disclosure is not an admission that it is prior art, especially any reference that has a publication date after the priority date of this application. The disclosure of all patents, patent applications, and publications cited in the disclosure are hereby incorporated by reference, to the extent that they provide exemplary, procedural, or other details supplementary to the disclosure.

While several embodiments have been provided in the present disclosure, it may be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and may be made without departing from the spirit and scope disclosed herein.

What is claimed is:

1. A method implemented by a user-portable mobile device for recommending audio to a user of the user-portable mobile device, the method comprising:
acquiring one or more measurements from at least one biometric sensor to obtain biometric information of the user;
determining, based on the biometric information, a biometric identifier as a classification of a biometric state of the user;
mapping the biometric identifier to a mood classifier to generate an audio selection, wherein the mood classifier identifies a particular mood from a plurality of moods based on the biometric identifier, and wherein the audio selection is associated with the particular mood;
modeling the audio selection based on an activity identifier, the biometric identifier, the mood classifier, user feedback, a location, time patterns, a motion status, and a current activity; and
producing the audio selection associated with the particular mood to the user through an output of the user-portable mobile device, wherein the output can be in the form of a signal or sound from a speaker.

2. The method of claim 1, further comprising:
updating, using a machine-learning algorithm, the mapping of the biometric identifier to the mood classifier based on user feedback, wherein the user feedback indicates a preference of the user regarding previous audio selections for the user; and
playing future audio selections to the user based on the previous audio selections via the updated mapping.

3. The method of claim 2, further comprising:
acquiring physical motion data of the user from at least one motion sensor; and
determining, based on the physical motion data, the activity identifier as a classification of physical motion of the user,
wherein the activity identifier and the biometric identifier are mapped to the mood classifier.

4. The method of claim 3, wherein the user-portable mobile device stores a mapping of each of a plurality of activity identifiers to a corresponding one of a plurality of biometric identifiers.

5. The method of claim 3, wherein the classification of the physical motion is one of a plurality of physical activities.

6. The method of claim 5, wherein the plurality of physical activities comprises one or more of standing, walking, running, biking, dancing, and skating.

7. The method of claim 1, wherein the biometric information of the user includes at least one of heart rate, skin temperature, perspiration level, oxygen level, brain wave, actigraphy sleep pattern, and electrocardiography (ECG).

8. A user-portable mobile device comprising:
a memory configured to store executable instructions;
a processor coupled to the memory and at least one biometric sensor, wherein the processor is configured to:
acquire biometric information of a user from the at least one biometric sensor;
determine, based on the biometric information, a biometric identifier as a classification of a biometric state of the user;
map the biometric identifier to a mood classifier to generate an audio selection, wherein the mood classifier identifies a particular mood from a plurality of moods, and wherein the audio selection is associated with the particular mood;
model the audio selection based on an activity identifier, the biometric identifier, the mood classifier, user feedback, a location, time patterns, a motion status, and a current activity; and
play the audio selection associated with the particular mood to the user through an output of the user-portable mobile device.

9. The user-portable mobile device of claim 8, wherein the processor is further configured to:
update, using a machine-learning algorithm, the mapping of the biometric identifier to the mood classifier based on user feedback, wherein the user feedback indicates a preference of the user regarding previous audio selections for the user; and
play future audio selections to the user based on the previous audio selections via the updated mapping.

10. The user-portable mobile device of claim 9, wherein the processor is further coupled to at least one motion sensor, and wherein the processor is further configured to:
acquire physical motion data of the user from at least one motion sensor; and
determine, based on the physical motion data, the activity identifier as a classification of physical motion of the user,
wherein the activity identifier and the biometric identifier are mapped to the mood classifier.

11. The user-portable mobile device of claim 10, further comprising a storage configured to store the mapping of the activity identifier and the biometric identifier to the mood classifier.

12. The user-portable mobile device of claim 10, wherein the classification of the physical motion is one of a plurality of physical activities, and wherein the plurality of physical activities comprises one or more of standing, walking, running, biking, dancing, and skating.

13. A computer program product comprising computer executable instructions stored on a non-transitory computer readable medium such that when executed by a processor cause a user-portable mobile device to:
acquire one or more measurements from at least one sensor to obtain physical condition data of a user using the user-portable mobile device, wherein the physical condition data includes physical motion data and biometric information of the user;
determine, based on the biometric information, a biometric identifier as a classification of a biometric state of the user;
determine, based on the physical motion data, an activity identifier as a classification of physical motion of the user;
map the activity identifier and the biometric identifier to a mood classifier to generate an audio selection, wherein the mood classifier identifies a particular mood from a plurality of moods, and wherein the audio selection is associated with the particular mood;
model the audio selection based on the activity identifier, the biometric identifier, the mood classifier, user feedback, a location, time patterns, a motion status, and a current activity; and
play the audio selection associated with the particular mood to the user through an output of the user-portable mobile device.

14. The computer program product of claim 13, wherein the processor further causes the user-portable mobile device to:
update, using a machine-learning algorithm, the mapping of the activity identifier and the biometric identifier to the mood classifier based on user feedback, wherein the user feedback indicates a preference of the user regarding previous audio selections to the user; and
play future audio selections to the user based on the previous audio selections via the updated mapping.

15. The computer program product of claim 13, wherein the physical condition data includes at least one of the physical motion data and the biometric information of the user.

16. The computer program product of claim 13, wherein the physical condition data is a combination of the physical motion data and the biometric information of the user, wherein the physical motion data is acquired from at least one motion sensor, and wherein the biometric information is acquired from at least one biometric sensor.

17. The computer program product of claim 13, wherein the classification of the physical motion is one of a plurality of physical activities, and wherein the plurality of physical activities comprises one or more of standing, walking, running, biking, dancing, and skating.

\* \* \* \* \*